US 9,728,069 B2

(12) United States Patent
Bolling

(10) Patent No.: US 9,728,069 B2
(45) Date of Patent: Aug. 8, 2017

(54) HAND CLEANLINESS

(71) Applicant: BioVigil, LLC, Ann Arbor, MI (US)

(72) Inventor: Steven F. Bolling, Ann Arbor, MI (US)

(73) Assignee: BioVigil Hygience Technologies, LLC, Ann Arbor, MI (US)

( * ) Notice: Subject to any disclaimer, the term of this patent is extended or adjusted under 35 U.S.C. 154(b) by 0 days.

(21) Appl. No.: 14/689,701

(22) Filed: Apr. 17, 2015

(65) Prior Publication Data

US 2015/0228182 A1   Aug. 13, 2015

Related U.S. Application Data

(63) Continuation of application No. 13/184,988, filed on Jul. 18, 2011, now Pat. No. 9,013,312, which is a continuation of application No. 12/614,822, filed on Nov. 9, 2009, now Pat. No. 7,982,619, which is a continuation of application No. 11/353,746, filed on Feb. 14, 2006, now Pat. No. 7,616,122, which is a continuation-in-part of application No. 11/157,094, filed on Jun. 20, 2005, now Pat. No. 7,286,057.

(51) Int. Cl.
*G08B 21/24*     (2006.01)
*G07C 9/00*      (2006.01)
*G08B 23/00*     (2006.01)

(52) U.S. Cl.
CPC ....... *G08B 21/245* (2013.01); *G07C 9/00031* (2013.01); *G08B 23/00* (2013.01); *G07C 2009/00095* (2013.01)

(58) Field of Classification Search
CPC .. G08B 21/245; G08B 23/00; G07C 9/00031; G07C 2009/00095
See application file for complete search history.

(56) References Cited

U.S. PATENT DOCUMENTS

| | | |
|---|---|---|
| 4,354,292 A | 10/1982 | Telestad et al. |
| 4,370,983 A | 2/1983 | Lichtenstein |
| 4,606,085 A | 8/1986 | Davies |
| 4,706,493 A | 11/1987 | Chang et al. |
| 4,782,334 A | 11/1988 | Meaney |
| 5,202,666 A | 4/1993 | Knippscheer |
| 5,366,896 A | 11/1994 | Margrey et al. |
| 5,373,852 A | 12/1994 | Harrison et al. |
| 5,412,816 A | 5/1995 | Paterson et al. |
| 5,428,213 A | 6/1995 | Kurihara |
| 5,441,047 A | 8/1995 | David et al. |
| 5,544,649 A | 8/1996 | David et al. |
| 5,606,159 A | 2/1997 | Kurihara |
| 5,610,589 A | 3/1997 | Evans et al. |
| 5,670,945 A | 9/1997 | Applonie |
| 5,685,262 A | 11/1997 | Stevenson |
| 5,771,925 A | 6/1998 | Lewandowski |
| 5,793,653 A | 8/1998 | Segal |
| 5,808,553 A | 9/1998 | Cunningham |
| 5,812,059 A | 9/1998 | Shaw et al. |
| 5,870,015 A | 2/1999 | Hinkel |
| 5,900,067 A | 5/1999 | Jones |
| 5,900,801 A | 5/1999 | Heagle et al. |

(Continued)

*Primary Examiner* — Hongmin Fan
(74) *Attorney, Agent, or Firm* — Fish & Richardson P.C.

(57) ABSTRACT

Among other things, an entry monitor has circuitry to detect when a person enters a monitored space and an indicator perceptible to other people in the space to indicate a cleanliness state of the hands of the person who has entered the space.

18 Claims, 5 Drawing Sheets

(56) References Cited

U.S. PATENT DOCUMENTS

Figure 1:
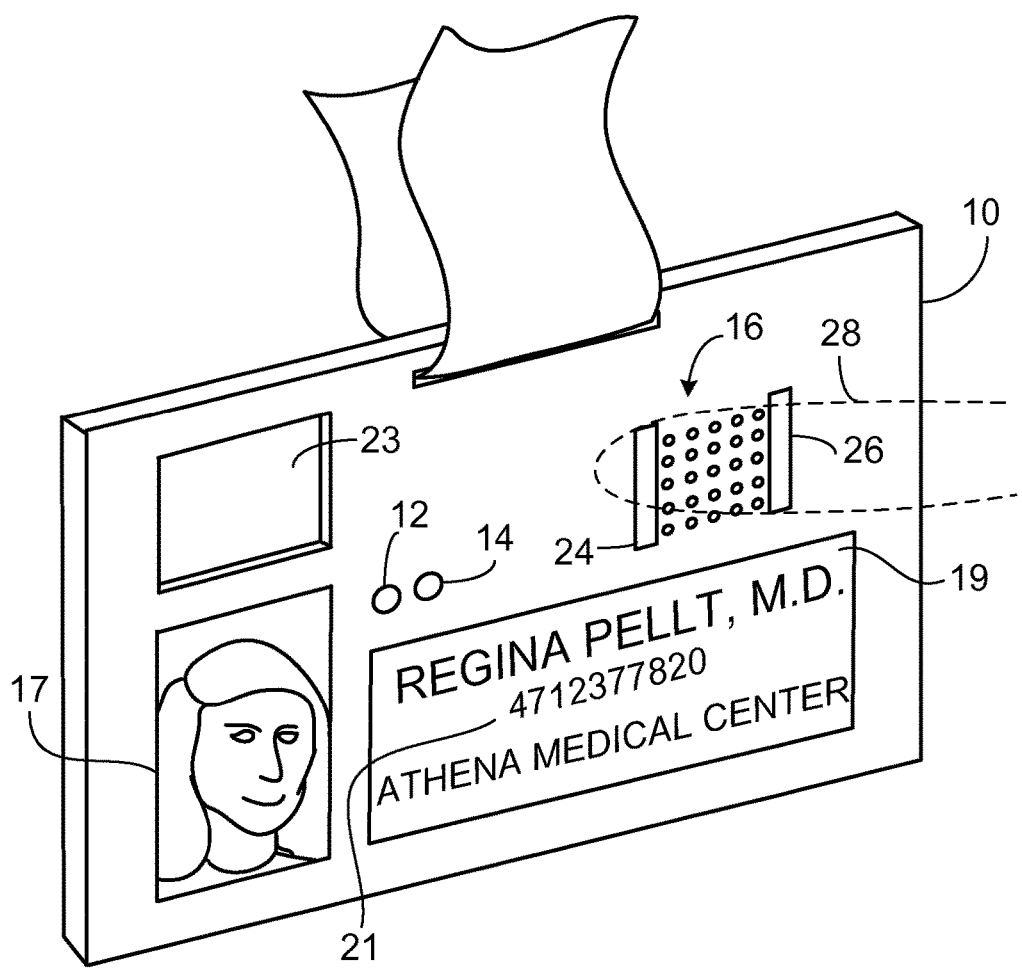

| | | | |
|---|---|---|---|
| 5,914,247 A | 6/1999 | Casey et al. |
| 5,939,974 A | 8/1999 | Heagle et al. |
| 5,943,713 A | 8/1999 | Paterson et al. |
| 5,945,910 A | 8/1999 | Gorra |
| 5,952,924 A | 9/1999 | Evans et al. |
| 5,954,069 A | 9/1999 | Foster |
| 5,966,753 A | 10/1999 | Gauthier et al. |
| 5,992,430 A | 11/1999 | Chardack et al. |
| 6,001,127 A | 12/1999 | Schoon et al. |
| 6,009,333 A | 12/1999 | Chaco |
| 6,029,293 A | 2/2000 | Patterson et al. |
| 6,029,600 A | 2/2000 | Davis |
| 6,032,071 A | 2/2000 | Binder |
| 6,038,331 A | 3/2000 | Johnson |
| 6,125,482 A | 10/2000 | Foster |
| 6,131,587 A | 10/2000 | Chardack et al. |
| 6,190,326 B1 | 2/2001 | McKinnon et al. |
| 6,236,317 B1 | 5/2001 | Cohen et al. |
| 6,236,953 B1 | 5/2001 | Segal |
| 6,245,206 B1 | 6/2001 | Anderson et al. |
| 6,246,330 B1 | 6/2001 | Nielsen |
| 6,278,372 B1 | 8/2001 | Velasco et al. |
| 6,347,724 B1 | 2/2002 | Chen et al. |
| 6,355,030 B1 | 3/2002 | Aldrich et al. |
| 6,375,038 B1 | 4/2002 | Daansen et al. |
| 6,392,546 B1 | 5/2002 | Smith |
| 6,404,837 B1 | 6/2002 | Thompson et al. |
| 6,417,773 B1 | 7/2002 | Vlahos et al. |
| 6,426,225 B1 | 7/2002 | Lewis et al. |
| 6,426,701 B1 * | 7/2002 | Levy | G08B 21/24 137/552.7 |
| 6,431,400 B1 | 8/2002 | O'Maley et al. |
| 6,468,800 B1 | 10/2002 | Stylli et al. |
| 6,471,087 B1 | 10/2002 | Shusterman |
| 6,542,568 B1 | 4/2003 | Howes, Jr. et al. |
| 6,547,130 B1 | 4/2003 | Shen |
| 6,572,564 B2 | 6/2003 | Ito et al. |
| 6,592,822 B1 | 7/2003 | Chandler |
| 6,605,038 B1 | 8/2003 | Teller et al. |
| 6,633,772 B2 | 10/2003 | Ford et al. |
| 6,687,190 B2 | 2/2004 | Momich et al. |
| 6,702,826 B2 | 3/2004 | Liddicoat et al. |
| 6,727,818 B1 | 4/2004 | Wildman et al. |
| 6,748,281 B2 | 6/2004 | Alsio |
| 6,757,898 B1 | 6/2004 | Ilsen et al. |
| 6,776,791 B1 | 8/2004 | Stallings et al. |
| 6,790,231 B2 | 9/2004 | Liddicoat et al. |
| 6,814,816 B2 | 11/2004 | Achar et al. |
| 6,847,913 B2 | 1/2005 | Wigley et al. |
| 6,867,698 B2 | 3/2005 | Herbert et al. |
| 6,882,273 B2 | 4/2005 | Kano |
| 6,882,278 B2 | 4/2005 | Winings et al. |
| 6,883,563 B2 | 4/2005 | Smith |
| 6,895,338 B2 | 5/2005 | Hsuing et al. |
| 6,913,608 B2 | 7/2005 | Liddicoat et al. |
| 6,929,607 B2 | 8/2005 | Lipman |
| 6,942,694 B2 | 9/2005 | Liddicoat et al. |
| 6,943,678 B2 | 9/2005 | Muirhead |
| 6,964,638 B2 | 11/2005 | Theodoracopulos et al. |
| 6,965,312 B2 | 11/2005 | Lerg |
| 6,967,576 B2 | 11/2005 | Hayes et al. |
| 6,975,231 B2 | 12/2005 | Lane et al. |
| 7,007,698 B2 | 3/2006 | Thornton |
| 7,015,816 B2 | 3/2006 | Wildman et al. |
| 7,020,508 B2 | 3/2006 | Stivoric et al. |
| 7,024,236 B2 | 4/2006 | Ford et al. |
| 7,034,677 B2 | 4/2006 | Steinthal et al. |
| 7,034,691 B1 | 4/2006 | Rapaport et al. |
| 7,045,673 B1 | 5/2006 | Batich et al. |
| 7,063,722 B2 | 6/2006 | Marquez |
| 7,069,444 B2 | 6/2006 | Lowensohn et al. |
| 7,074,183 B2 | 7/2006 | Castellanos |
| 7,081,131 B2 | 7/2006 | Thornton |
| 7,087,015 B1 | 8/2006 | Comrie et al. |
| 7,095,501 B2 | 8/2006 | Lambert et al. |
| 7,098,793 B2 | 8/2006 | Chung |
| 7,107,631 B2 | 9/2006 | Lang et al. |
| 7,122,005 B2 | 10/2006 | Shusterman |
| 7,132,940 B2 | 11/2006 | Ehben et al. |
| 7,191,097 B1 | 3/2007 | Lee et al. |
| 7,228,874 B2 | 6/2007 | Bolderheij et al. |
| 7,236,097 B1 * | 6/2007 | Cunningham | G08B 21/245 340/309.7 |
| 7,242,306 B2 | 7/2007 | Wildman et al. |
| 7,242,307 B1 | 7/2007 | LeBlond et al. |
| 7,267,798 B2 | 9/2007 | Chandler |
| 7,271,728 B2 | 9/2007 | Taylor et al. |
| 7,286,057 B2 | 10/2007 | Bolling |
| 7,293,645 B2 | 11/2007 | Harper et al. |
| 7,482,936 B2 | 1/2009 | Bolling |
| 7,616,122 B2 | 11/2009 | Bolling |
| 7,936,275 B2 | 5/2011 | Bolling |
| 7,982,619 B2 | 7/2011 | Bolling |
| 8,502,681 B2 | 8/2013 | Bolling et al. |
| 2002/0000449 A1 * | 1/2002 | Armstrong | A47K 5/1217 222/52 |
| 2002/0019586 A1 | 2/2002 | Teller et al. |
| 2002/0082177 A1 | 6/2002 | Tabaac |
| 2002/0095073 A1 | 7/2002 | Jacobs et al. |
| 2002/0132214 A1 | 9/2002 | Mattson et al. |
| 2002/0135486 A1 | 9/2002 | Brohagen et al. |
| 2002/0180605 A1 | 12/2002 | Ozguz et al. |
| 2003/0019536 A1 | 1/2003 | Smith |
| 2003/0026549 A1 | 2/2003 | Ellis et al. |
| 2003/0030562 A1 | 2/2003 | Lane et al. |
| 2003/0130567 A1 | 7/2003 | Mault et al. |
| 2003/0147925 A1 | 8/2003 | Sawan et al. |
| 2003/0164456 A1 | 9/2003 | Petrich et al. |
| 2003/0179224 A1 | 9/2003 | Alsio |
| 2003/0220215 A1 | 11/2003 | Manske |
| 2004/0034289 A1 | 2/2004 | Teller et al. |
| 2004/0067544 A1 | 4/2004 | Vogel et al. |
| 2004/0090333 A1 | 5/2004 | Wildman et al. |
| 2004/0092965 A1 | 5/2004 | Parihar |
| 2004/0135684 A1 | 7/2004 | Steinthal et al. |
| 2004/0148019 A1 | 7/2004 | Vidlund et al. |
| 2004/0148020 A1 | 7/2004 | Vidlund et al. |
| 2004/0150527 A1 | 8/2004 | Harper et al. |
| 2004/0155772 A1 | 8/2004 | Medema et al. |
| 2004/0172063 A1 | 9/2004 | Li et al. |
| 2004/0186565 A1 | 9/2004 | Schreck |
| 2004/0193261 A1 | 9/2004 | Berreklouw |
| 2004/0230809 A1 | 11/2004 | Lowensohn et al. |
| 2004/0243104 A1 | 12/2004 | Seddon |
| 2004/0243230 A1 | 12/2004 | Navia et al. |
| 2005/0004665 A1 | 1/2005 | Aklog |
| 2005/0004668 A1 | 1/2005 | Aklog et al. |
| 2005/0006559 A1 | 1/2005 | Smith |
| 2005/0035862 A1 | 2/2005 | Wildman et al. |
| 2005/0038741 A1 | 2/2005 | Bonalle et al. |
| 2005/0049157 A1 | 3/2005 | MacDonald et al. |
| 2005/0077348 A1 * | 4/2005 | Hendrick | G06K 7/00 235/380 |
| 2005/0079637 A1 | 4/2005 | Wilhelm et al. |
| 2005/0088299 A1 | 4/2005 | Bandy et al. |
| 2005/0090414 A1 | 4/2005 | Rich |
| 2005/0134465 A1 | 6/2005 | Rice et al. |
| 2005/0191326 A1 | 9/2005 | Melker |
| 2005/0227880 A1 | 10/2005 | Shiloach et al. |
| 2005/0231373 A1 | 10/2005 | Lynn et al. |
| 2005/0233918 A1 | 10/2005 | Rich |
| 2005/0233919 A1 | 10/2005 | Rich |
| 2006/0025855 A1 | 2/2006 | Lashinski et al. |
| 2006/0067545 A1 | 3/2006 | Lewis et al. |
| 2006/0071799 A1 | 4/2006 | Verdiramo |
| 2006/0111620 A1 | 5/2006 | Squilla et al. |
| 2006/0132316 A1 | 6/2006 | Wildman et al. |
| 2006/0184240 A1 | 8/2006 | Jimenez et al. |
| 2006/0184241 A1 | 8/2006 | Marquez |
| 2006/0214000 A1 | 9/2006 | Lapstun et al. |
| 2006/0240397 A1 | 10/2006 | Lynn et al. |
| 2006/0272361 A1 | 12/2006 | Snodgrass |
| 2006/0273915 A1 | 12/2006 | Snodgrass |
| 2007/0005129 A1 | 1/2007 | Damm et al. |

(56) References Cited

U.S. PATENT DOCUMENTS

| | | |
|---|---|---|
| 2007/0008146 A1 | 1/2007 | Taylor et al. |
| 2007/0080801 A1* | 4/2007 | Weismiller ............. A61B 5/411 340/539.13 |
| 2008/0031838 A1 | 2/2008 | Bolling |
| 2011/0025509 A1* | 2/2011 | Brow ....................... A47K 5/06 340/573.1 |
| 2012/0062378 A1 | 3/2012 | Bolling |
| 2012/0068843 A1 | 3/2012 | Bolling |

* cited by examiner

HAND CLEANLINESS

This is a continuation of U.S. patent application Ser. No. 13/184,988, entitled Hand Cleanliness, filed Jul. 8, 2011; which is a continuation of U.S. patent application Ser. No. 12/614,822, entitled Hand Cleanliness, filed Nov. 9, 2009 (now U.S. Pat. No. 7,982,619); which is a continuation of U.S. patent application Ser. No. 11/353,746, entitled Hand Cleanliness, filed Feb. 14, 2006 (now U.S. Pat. No. 7,616, 122); which is a continuation-in-part of U.S. patent application Ser. No. 11/157,094, entitled Hand Cleanliness, filed Jun. 20, 2005 (now U.S. Pat. No. 7,286,057). The disclosure of the prior applications are considered part of (and are incorporated by reference in) the disclosure of this application.

BACKGROUND

This description relates to hand cleanliness.

Health care workers, food handlers, and others ought to clean their hands frequently and thoroughly, but they often don't. Better hand cleaning habits can be promoted by governmental regulations, company rules, social pressure, and technology. Techniques that have been proposed for improving cleaning habits include the use of special cleaning agents as well as mechanisms and electronic devices to regulate, monitor, and report on how frequently and how effectively people clean their hands.

SUMMARY

In one general aspect, an electronic sensor is configured to be carried by a person and to be used by the person to detect a cleanliness state of the person's hands, and a holder for the electronic sensor has a structure to temporarily receive an identification badge of the person.

Implementations may include one or more of the following features. The badge and the holder contain respective communication elements to permit information about a cleanliness test performed by the person using the electronic sensor to be communicated to the badge. The badge includes a unique identifier of the person that can be read electronically.

In one general aspect, an electronic sensor is carried by a person or mounted in a stationary position accessible to a person's hands, and is used by the person to detect a cleanliness state of the person's hands. Circuitry detects and provides an alert when the electronic sensor is nearing the end of its useful life.

Implementations may include one or more of the following features. The circuitry includes a counter of a number of times the sensor is used. The sensor comprises an ethanol sensor.

In one general aspect, the sensor includes a chemical sensor that is sensitive to a cleaning material other than ethanol.

In one general aspect, the sensor includes a ceramic sensor for ethanol.

In one general aspect, circuitry counts a number of times a person has run a cleanliness test using the sensor.

Implementations may include one or more of the following features. A circuit communicates the count wirelessly to a reader for reporting to a third party.

In one general aspect, a storage device is coupled to the sensor to store information about the frequency, timing, and/or results of cleanliness measurements performed by the user using the electronic sensor.

In one general aspect, a monitor has detection circuitry to detect a presence of one or more people in a monitored space and reporting circuitry to report a cleanliness state of hands of the people in the monitored space, based on information provided by one or more sensors used to sense a disinfecting agent on the hands of the people.

Implementations may include one or more of the following features. The detection circuitry detects the presence of one or more people by wireless communication with a device held on or by the person. The wireless communication comprises RFID communication. The monitored space comprises a room in a health care facility. The sensors are worn by one or more of the people. The sensors are associated with the monitor. The sensors sense ethanol. The cleanliness state is reported with respect to each of the people separately. The cleanliness state is reported to everyone in the space.

In one general aspect, an entry monitor has circuitry to detect when a person enters a monitored space and an indicator perceptible to other people in the space to indicate a cleanliness state of the hands of the person who has entered the space.

Implementations may embody one or more of the following features. The circuitry to detect when a person enters a monitored space includes a wireless communication element. The indicator comprises a light. The indicator can indicate a disinfected state and a non-disinfected state. The indicator is set to indicate a non-disinfected state of the person's hands when the person enters the space, whether or not the person's hands are then in a disinfected state. The indicator is set to switch to indicate a disinfected state only after the person successfully establishes the disinfected state using a sensor that senses a presence of a disinfectant. The indicator is set to switch to indicate a disinfected state only after all of the people who have entered the room have successfully established the disinfected state using one or more sensors that sense a presence of a disinfectant. The circuitry obtains, from a device worn by the person, information identifying the person uniquely.

In one general aspect, badges worn by people who enter a space contain indicia that uniquely identify the respective people who wear the badges, one or more sensors sense a presence of a disinfectant material on hands of each of the people, and a monitor detects the presence of one or more of the people in a space and indicates a cleanliness state of the people in the space.

In one general aspect, system monitors cleanliness states of hands of people who are moving from space to space in a facility; the system includes circuitry to identify each of the people uniquely in more than one of the spaces of the facility, circuitry to test the cleanliness state of the hands of one or more of the people in one or more of the spaces, and to associate the tests with the identities of the people, and a communication network to exchange information about the tested cleanliness of the people in the spaces of the facility from time to time and to provide related reports to a third party.

In one general aspect, on a device that is worn or carried by a person and contains an identifier uniquely associated with the person, a record is stored of tests performed by the person on a sensor to determine a cleanliness state of the hands of the person at a succession of test times. In general, in one aspect, the invention features an electronic sensor configured to be carried by a person and to be used by the person to detect a cleanliness state of the person's hands.

Implementations may include one or more of the following features. There is also a device configured (a) to identify the person, (b) to be associated with the electronic sensor, and (c) to be carried by the person. There is also a device configured to be associated with the electronic sensor and to provide an indication of the cleanliness state of the person's hands. The indicating device is configured to be carried by the person, and the indicating device and the sensor together are capable of detecting a cleanliness state of the person's hands and providing an indicator of the cleanliness state, without requiring cooperation between the apparatus and any device external to the apparatus. There is also a circuit to control how long after the state of the person's hands has determined to be clean, the state is presumed no longer to be clean.

In general, in another aspect, the invention features a single unit that includes an electronic sensor to be used by a person to detect a cleanliness state of the person's hands, and a device to provide an indication of the cleanliness state of the person's hands.

In general, in another aspect, the invention features a single unit that includes an electronic sensor to be used by a person to detect a cleanliness state of the person's hands, and a device to identify the person.

In general, in another aspect, the invention features a circuit that is configured to control how long after a cleanliness state of a person's hands has been determined to be clean, the state is presumed no longer to be clean.

Implementations may include one or more of the following features. The electronic sensor is configured to sense a presence or absence of a material indicative of the cleanliness state, for example, a vapor or alcohol. The cleanliness state comprises a disinfection state. The identification device comprises a badge. The identification device and the sensor are part of one unit. The electronic sensor, the identification device, and the indication device are part of one unit. The unit is configured to be worn by the person. The indication device comprises a visible indicator. The circuit comprises a countdown timer that is triggered in connection with the cleanliness state being determined to be clean. The circuit is part of the unit.

In general, in another aspect, the invention features a badge that includes indicia identifying a person who carries the badge, a sensor to be used to detect a cleanliness state of the person's hands, and a visible indicator to indicate to other people the cleanliness state of the person's hands.

In general, in another aspect, the invention features a person using an electronic sensor carried by the person to detect a cleanliness state of the person's hands.

In general, in another aspect, the invention features issuing a signal from a circuit to indicate how long after a state of a person's hands has been determined to be clean, the state is presumed no longer to be clean.

DETAILED DESCRIPTION

Figure 2:
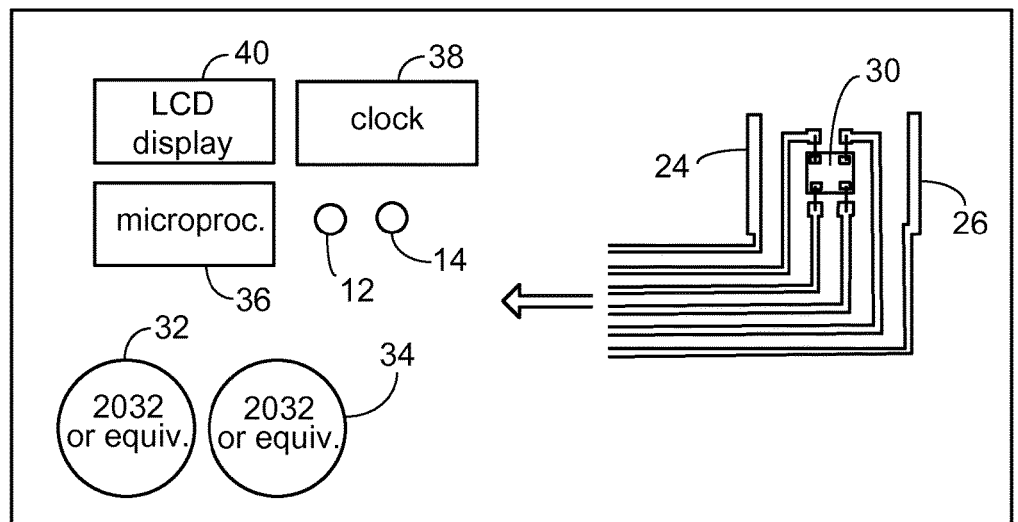
Figure 3:
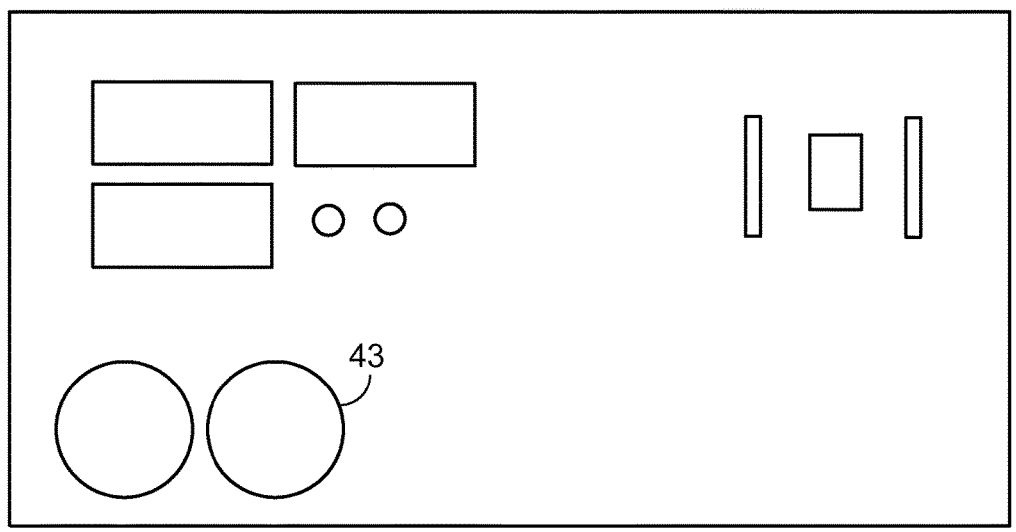
Figure 4:
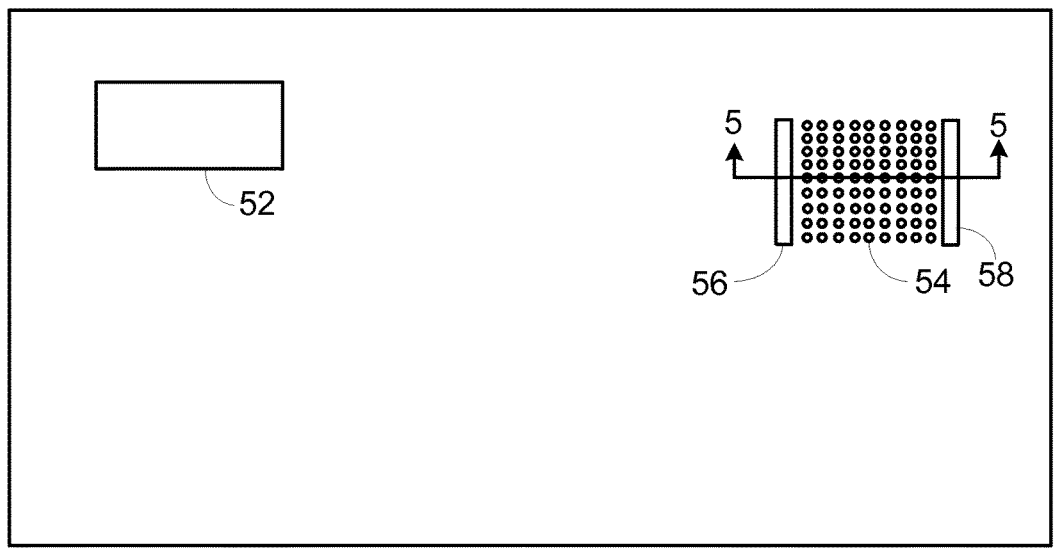
Figure 5:
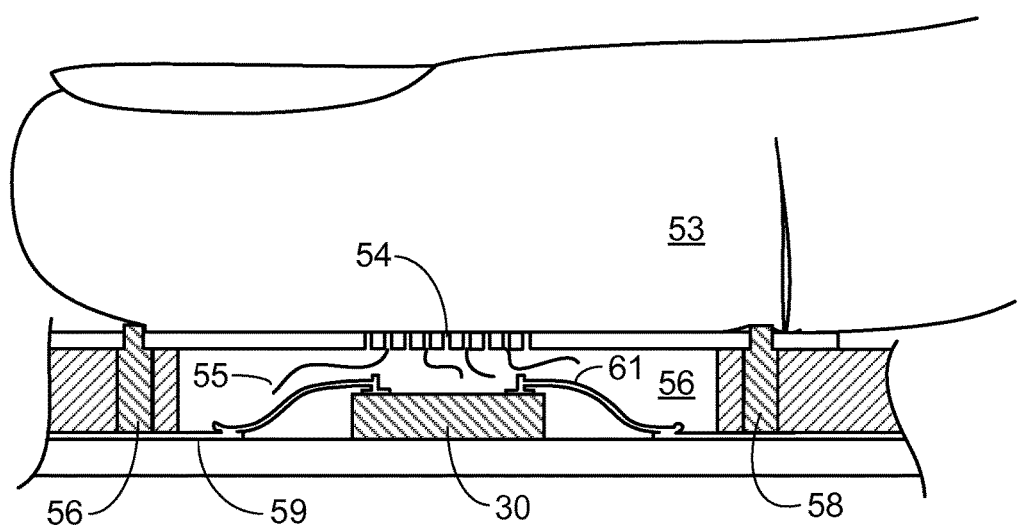
Figure 6:
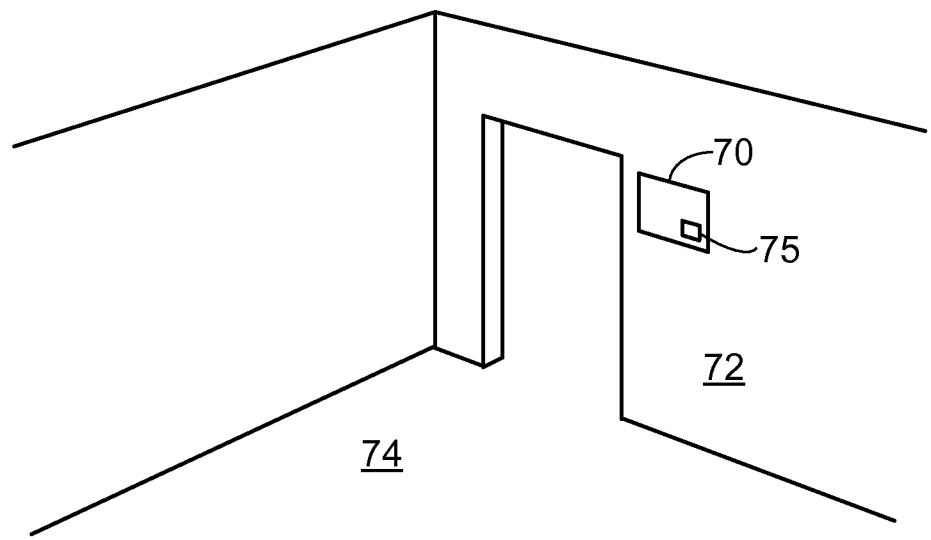
Figure 7:
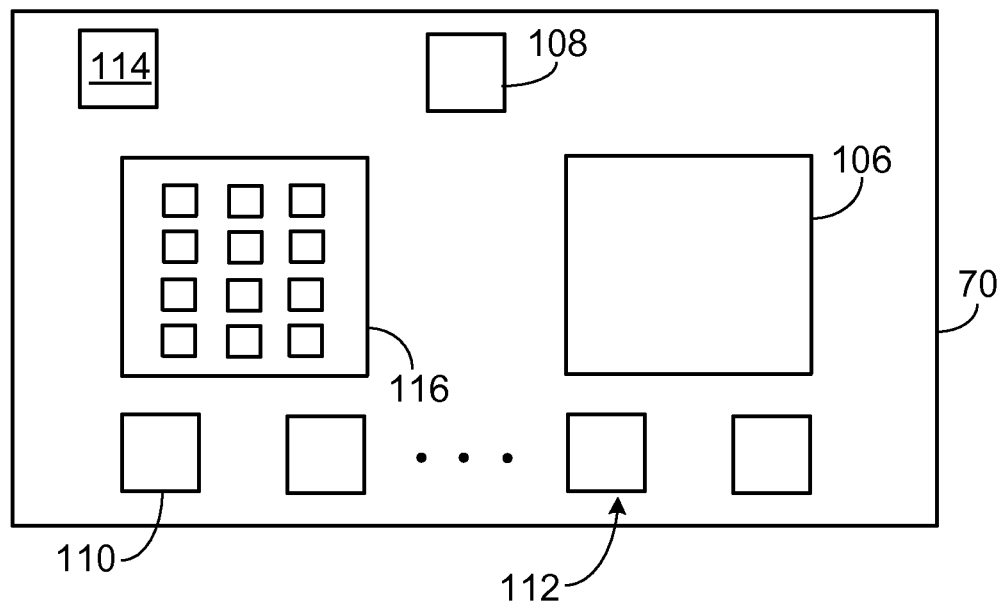
Figure 8:
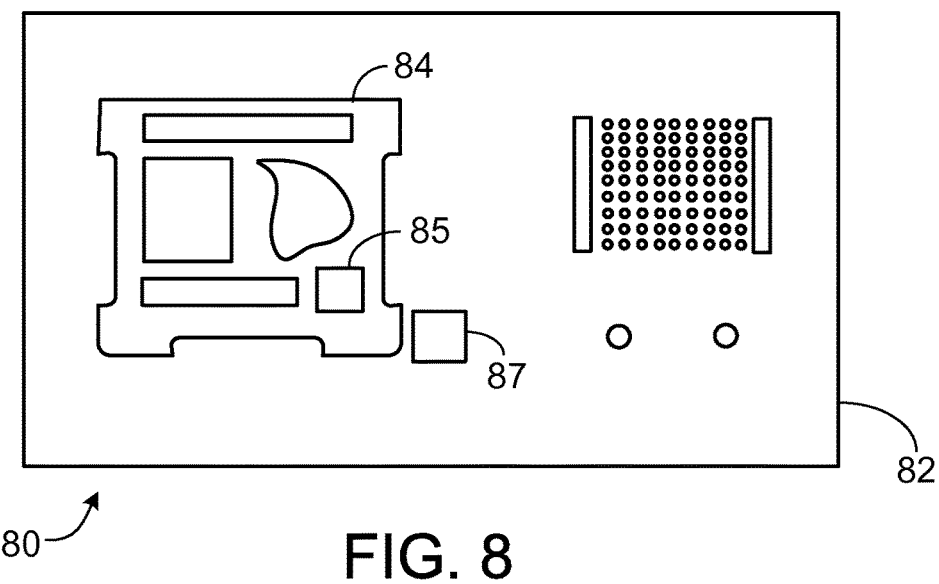
Figure 9:
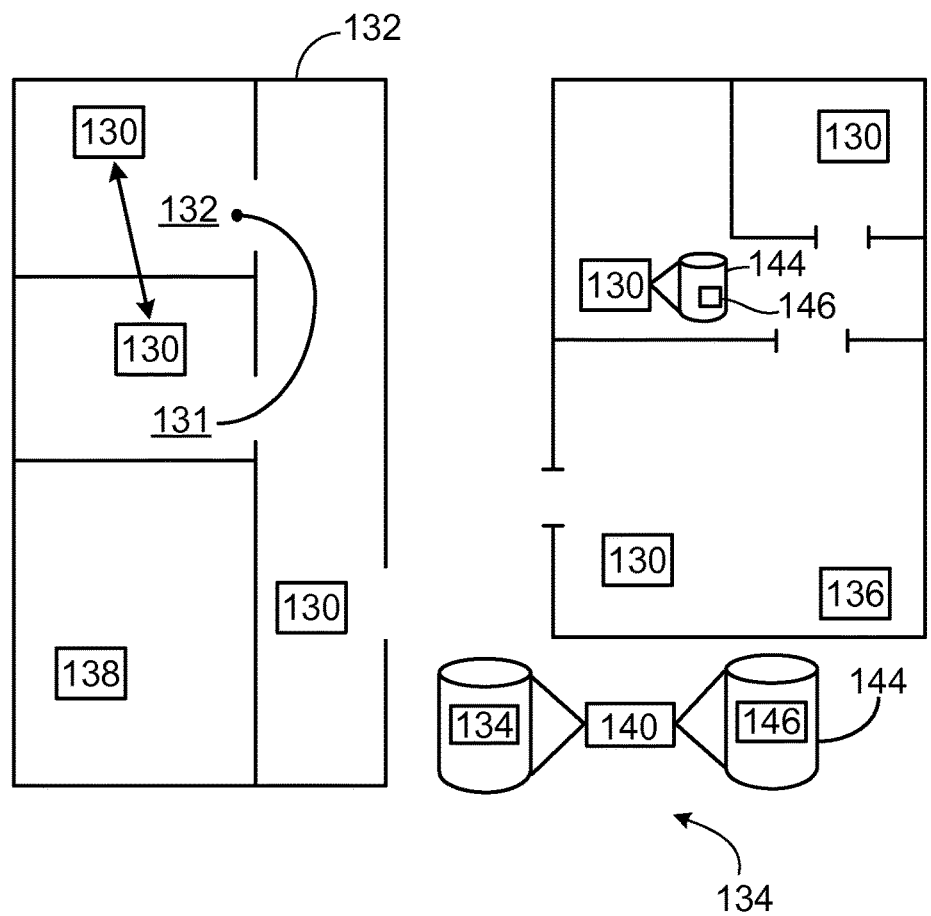

FIG. 1 is a perspective view of a badge.
FIGS. 2, 3, and 4 are schematic plan views of three layers of the badge.
FIG. 5 is a sectional side view of a chamber at 5-5 in FIG. 4.
FIG. 6 is a three-dimensional view of a space.
FIG. 7 shows a monitor.
FIG. 8 shows a badge in a badge holder.
FIG. 9 is a schematic view of a campus of buildings.

As shown in FIG. 1, in some examples, an identification badge 10 worn by a doctor has red and green lights 12, 14, that indicate that her hands are likely to be respectively in a clean (e.g., disinfected, green light) condition or in a not clean (e.g., not disinfected, red light) condition. The two lights are controlled by a control circuit (not shown in FIG. 1) based on (a) information derived from an ethanol sensor 16 in the badge, (b) signals from a timer (also not shown in FIG. 1) that tracks the passage of time after the circuit has determined that the hands are likely to be in a disinfected condition, and (c) the state of the logic implemented by the control circuit (also not shown). An LCD display 23 provides displayed information that can include the status of the badge, the control circuit, or the sensor; the time; the status of the cleanliness of the doctor's hands; and other information.

In addition to providing the disinfection determining function, the badge 10 can be of a shape and form and can display information sufficient to serve a conventional function of complying with government and institution regulations that require health care workers to carry visible identification. For example, the badge includes a photograph 17 of the doctor, and other information including the doctor's name 19 and identification number 21. A typical badge could be approximately credit-card size.

Because health care workers are required to carry such badges for other reasons, providing the disinfection determining function within the same badge make it more likely that the worker will use that function than if the function were provided in a separate device that the worker was expected to carry separately. In addition, because the badge worn by a worker must be visible to others in the health care environment, the feature of the badge that indicates whether the user's hands are clean or unclean will naturally be visible to others. Thus, the worker, merely by having to wear the badge, will be subjected to social pressure of peers, patients, and managers with respect to the cleanliness of the worker's hands. This makes the use of the disinfection determining feature of the badge and the improvement of cleanliness habits self-enforcing. The institution by whom the worker is employed need only provide badges that include those features without directly managing or monitoring their use.

A pair of electrodes 24, 26 on either side of the sensor is used to determine when a finger 28 or other part of the hand or other skin has been placed against the sensor. When skin of a finger or other part of the hand touches both electrodes, the resistance between them will decline. By measuring that resistance the control circuit can detect the presence of a finger.

The badge is used by the doctor in conjunction with disinfecting her hands using cleaners of the kind that include ethanol (for example, the liquid known by the name Purell available from GOJO Industries, Akron, Ohio, and which contains 62% ethyl alcohol). Such cleaners are considered to be more effective than soaps and detergents in killing bacteria and viruses and are widely used in health care and other environments. When the ethanol-based cleaner is rubbed on the skin of the hands, the ethanol kills the bacteria and viruses. The effect will last for several hours but eventually wears off. Ethanol is volatile and eventually evaporates from the skin, leaving the possibility (which increases over time) that live bacteria and viruses will again contaminate the skin from the air and from objects that are touched, for example.

The concentration of ethanol on the skin and the decay of that concentration from evaporation tend to determine the onset of subsequent contamination. In turn, the concentration of ethanol on the skin can be inferred by the concentration of ethanol vapor near the skin. By placing the skin near an ethanol detector for a short period of time, it is possible to determine the vapor concentration of ethanol and thus to infer the ethanol concentration on the skin and the disinfected state of the skin. When the current inferred concentration is above a threshold, it is possible to make an assumption about how long the hands will remain disinfected.

The badge can be used in the following way to improve the hand cleaning habits of the user.

In some simple examples, the badge can be configured to determine and display two different states: disinfected and not disinfected.

Except when the badge has recently enough (say within two or three hours) entered the disinfected state due to a measurement cycle in which an adequate concentration of ethanol vapor had been sensed, the badge will assume a default state of the user's skin of not disinfected. Thus, when the badge is first powered on, or reset, or the permitted time since a prior successful measurement has elapsed, the state becomes not disinfected. When the state is not disinfected the red light is lit and the word re-test is displayed on the LCD.

In some implementations, the badge can be made to switch from the not disinfected state to the disinfected state only by a successful ethanol measurement cycle. A successful cycle is one in which a finger or other part of the body is held in position over the sensor (touching both of the electrodes) for a period that is at least as long as a required measurement cycle (e.g., 30 seconds or 45 seconds or 60 seconds depending on the design of the circuit), and the concentration of ethanol vapor that passes from the skin into a measurement chamber of the sensor is high enough to permit an inference that the skin is disinfected.

Thus, when the doctor wipes her hands with the cleaner to disinfect them, she can then press one of her clean fingers against the sensor 16 and the two electrodes 24, 26, for, say, 60 seconds.

Touching of both of the electrodes simultaneously by the finger is detected by the control circuit which then begins the measurement cycle. The control circuit could start the red and green lamps to flash alternately and to continue to do so as an indication to the user that the electrodes are both being touched and that the measurement cycle is proceeding. At the end of the sensing cycle, the control circuit determines a level of concentration of ethanol and uses the level to determine whether the finger, and by inference, the hand of the doctor is disinfected. Each time a measurement cycle has been fully completed, the red and green lights may both be flashed briefly to signal that the cycle has ended and the finger may be removed.

The control circuit continually monitors the electrodes to determine when a finger or other skin is touching both of the electrodes. When that event is detected, a measurement cycle count down timer (which is initialized for the number of seconds needed to complete a measurement) is started. At the beginning of a cycle, a voltage is applied to the heater to begin to heat the sensor element. Initially the heater voltage may be set to a higher than normal value in order to shorten the initial action period described below. Then the heater voltage is reduced. At the end of the measurement cycle, a measurement voltage is applied across the series connection of the measurement cell and the series resistor, and the voltage across the series resistor is detected and compared to a threshold to determine whether the state should be set to disinfected or not disinfected.

When the control circuit determines that the hand is disinfected, the control circuit switches to the disinfected state, lights the green lamp (and turns off the red lamp), and displays the word clean on the LCD. In addition, upon the initiation of the disinfected state, the control circuit starts a re-test count down timer that is initially set to the period during which the skin is expected to remain disinfected (for example two hours).

If the control circuit is in the disinfected state and the user voluntarily performs another successful measurement cycle (for example, if, during the two hours after the prior successful measurement, she disinfects her hands again), the re-test count down timer is reset.

Anyone in the vicinity of the doctor who can see the lights or LCD is made aware of whether, according to the doctor's use of the badge, the doctor's hands are disinfected or not. People who find troubling the indication that a person's hands are not disinfected can complain to the person or to the employer, for example.

During the sensing cycle the doctor must keep her finger against the sensor for at least a certain period of time, say 60 seconds, to give the sensor and the control circuit time to obtain a good reading. If the doctor removes her finger before the end of the period, the control circuit remains in or switches to the not disinfected state and displays the word re-test on the LCD display.

If the doctor holds her finger against the sensor long enough to complete the sensing cycle, the results of the sensing cycle are displayed on the LCD and by lighting either the red light or the green light.

If the sensing cycle ends with a determination that the finger is not disinfected, the doctor can try again to apply enough of the cleaner to her hands to satisfy the circuit and can test the ethanol concentration again. And the cycle can be repeated until the disinfected state is determined.

In addition to causing the green light to be illuminated and the LCD to show clean, successfully completing an ethanol test also causes the control circuit to reset a count down timer (not shown in FIG. 1) to a predetermined period (say, two hours) after which it is assumed that the benefit of the ethanol treatment has worn off and the doctor's hands are no longer disinfected. When the timer times out at the end of the predetermined period, the control circuit turns off the green light, lights the red light, and changes the displayed word from clean to re-test. The red light stays on and the word re-test continues to be displayed until a successful ethanol test is performed by the doctor.

As shown in FIGS. 2, 3, and 4, the badge 10 can be fabricated by assembling three layers.

A bottom layer 29 (shown schematically in FIG. 2) contains a printed circuit 31 and components mounted on the circuit. The components include the sensor element 30 of the sensor, two thin batteries 32, 34, a microprocessor 36 (an example of the control circuit mentioned earlier), a clock 38 (an example of the timer circuit mentioned earlier that can be used both for the measurement count-down timer and for the re-test count-down timer), the two LED lamps 12, 14, and an LCD display device 40. The detailed interconnections of the devices mounted on the bottom layer are not shown in FIG. 2. The control circuit could be, for example, a PIC microcontroller available from Microchip Technology, Inc. of Chandler, Ariz.

A middle layer (shown schematically in FIG. 3) is thicker than the bottom and top layer and provides physical relief for the components mounted on the bottom layer. The patterns shown in FIG. 3 represent cutouts 43 or perforations in the middle layer.

A top layer 50 (shown schematically in FIG. 4) includes a non-perforated and non-printed clear region 52 to permit viewing of the LCD display. Space is left for adding a photograph and other information as show in FIG. 1. A perforated region 54 provides openings for passage of ethanol vapors into the badge and two perforations 56, 58 on opposite sides of the perforated region 54 accept the conductive electrodes that are used to detect the presence of a finger.

As shown in FIG. 5, the arrangement of the three layers in the vicinity of the sensor provides a sensing chamber 56. Ethanol vapors 55 pass from the finger 53 through the holes in perforated region 54 (which is shown as narrower than in FIG. 4) and into the chamber. Within the chamber is a tin oxide sensor element 30 (which includes an integral heater). The sensor element is connected by wire bonded connections 61 to circuit runs 59 on the bottom layer of the badge. The heater heats the vapors within the chamber and sensor element measures the concentration of ethanol.

Tin oxide sensors are small, low cost, and relatively low in power requirements. An example of a tin oxide ethanol sensor is the Model TGS 2620-M available from Figaro USA Inc. of Glenview, Ill., although other sensors available from other vendors could be used.

The sensor includes an integral heater and four connections, two for the sensor element, and two for the heater. By wiring a resistor in series with the element and measuring the voltage drop across the resistor, the control circuit can determine the amount of current flowing in the element and hence the resistance of the element which will vary with ethanol concentration.

Tin oxide sensors with heaters are subject to a so-called initial action that occurs when the sensors are not energized for a period and then are energized. The resistance of the sensor drops sharply during an initial period of energization, whether gases are present in the surrounding air or not. The longer the period of unenergized storage (up to about 30 days), the longer the period of the initial action. Therefore using tin oxide sensors in the badges requires a trade off between powering their operation for a period longer than the initial action but not so long that the energy drain caused by measurement cycles reduces the lifetime of the battery to an unacceptably short period. Experiments suggest that if the user keeps her finger in contact with the sensor for at least 20 or 30 seconds, the sensing of ethanol then begins to dominate the initial action and permits detection of the ethanol concentration. Other approaches may provide a shorter initial action (such as applying a larger voltage for the first few sections of operation and then the normal voltage after that).

The badge provides a simple, effective, portable, inexpensive way to confirm that the ethanol treatment has occurred no longer than, say, two hours ago, which likely means that the hands remain disinfected. No other external equipment is needed. The disinfection condition is apparent to anyone in the vicinity of the doctor, including patients, supervisors, regulators, and peers. The social pressure associated with being identified easily as not having disinfected hands is an effective way to improve the frequency and thoroughness of cleaning. The system does not force the doctor to comply. Compliance with cleaning rules and policies may remain less than perfect using the badges. Yet it is likely that the compliance will improve significantly. Any degree of improvement translates into reduced costs and injuries now associated with hands that have not been disinfected.

A wide variety of other implementations are within the scope of the following claims.

Although we sometimes have referred to use of the system by a doctor, it is also useful for a wide variety of other people, including other health care workers, clean room workers, and guests, consumers, vendors, employees, and other parties involved in any kind activity in which cleanliness of the hands or other parts of the body is important.

For example, although a simple matching of a measured ethanol concentration against a threshold can be used to determine simply whether the state should be disinfected or not disinfected, it is also possible to provide a more complicated analysis of measured concentration over time and a comparison of the measured concentration against dynamically selected thresholds.

More than two states would be possible, for example, to denote different levels of disinfection or to denote that longer periods of time may elapse before another measurement is required.

The length of time before a first measurement is considered stale and another measurement is required need not be based on an estimate of how long the ethanol on the skin will be effective, but can be based on an arbitrary period such as every hour.

The degree of accuracy and repeatability of the measurement of ethanol concentration may be traded with the cost and complexity of the circuitry needed to do the measurements. In some examples, the goal need not be to assure that the user's hands are thoroughly disinfected at all times. Rather, if the system encourages more frequent and more thorough cleaning to any noticeable degree, great benefits will result. Thus a very simple system may be quite useful and effective even though it may allow some users to cheat and may fail to determine the state accurately at all times.

Additional lights and displayed words may be used for a variety of purposes. The approach of the end of the disinfected period could be indicated by a yellow light to alert the user that a cleaning would soon be needed.

The lights and LCD display could be supplemented with or replaced by audible alerts for all functions or some of them.

In some examples, not all of the circuitry need be mounted in a single badge. Some of the circuitry could be located in a different piece of equipment. For example, a sensor used in common by many people may be mounted on a wall and convey (say by wireless communication) the measured concentration of ethanol to the badge, which would then determine the state and indicate that state through lights and on the LCD. By separating the two, the badge could be lower cost, the sensor could be more complex and accurate, and the sensor could be located at places where the disinfectant solution is dispensed. Fewer sensors would be needed.

Each badge could itself be split into two components that communicate with each other wirelessly or by wire. For example, a sensor module could be located in the user's pocket, while the badge contains only the logic circuitry.

The cleaning agent that is being measured need not be limited to ethanol but could include combinations of ethanol with other materials or other materials in the absence of ethanol; an appropriate sensor for the other materials would be used.

The badge could include clips, hook and loop fasteners, chains, pins, ribbons, and belt loops, and other devices to hold the badge on the user.

The device need not take the form of a badge but could be an ID device that attaches to a belt, a lapel, any other article of clothing, and other parts of the body including an arm, a leg, or a neck.

Instead of integrating the badge, sensor, and indicators in one unit, the badge could be an already existing badge of the kind used in hospitals, for example, to identify employees. Such badges often include names, photographs, and magnetic stripes or bar codes that can be swiped on readers. As shown in FIG. 8, the device 80 could take the form of a holder 82 in which the existing badge 84 could be held. The device would then contain all of the other elements except those that appear on the badge. Arranging for a separate badge and badge holder has a number of advantages. The badge can be removed and used and swiped independently of the device. The badge can be replaced separately without requiring a replacement of the device electronics. Existing badge equipment and technology can continue to be used. In some examples, the badge could be designed to couple electronically to the holder using, for example, RFID technology with an RFID element 85 in the badge and an RFID transceiver 87 in the holder. When the badge is placed in the holder, the holder recognizes the identification of the user and other information.

In some examples, the badge, the holder, and the RFID transceiver 87 could be arranged differently. For example, the RFID transceiver could be located on a different device worn by the user while the badge could remain mounted on the holder.

The badge could be powered by photovoltaic cells using ambient light instead of a battery.

Although two different lights could be used to indicate the disinfected and not disinfected conditions, a single light that can change color could also be used, saving cost and space.

Because the ethanol sensor has a lifetime that is limited by the number of test cycles, the badge can include a circuit that counts the number of tests performed and illuminates a warning light or provides some other indicator when the sensor is reaching the end of its useful life.

Other types of ethanol sensors can be used. One such sensor comprises a ceramic chip but is considerably more expensive than the sensors described earlier.

Although ethanol and an ethanol sensor form the basis of some of the examples described here, other disinfectants (for example, trichlosan) may also be used provided that effective sensors are available for them.

In general, in addition to triggering a change in state of the badge after a period elapses, it is also useful to maintain a count of the number of times a person has run a test (sometimes called the number of taps) using the sensor in a given period of time. The badge can contain a counter that keeps track of the number of taps and determines the count per 24 hours. This number can then be reported to the person's employer or to regulatory agencies as evidence of good cleanliness practices in an institution. For reporting purposes, the number of counts can be communicated to a reader by RFID technology, or any other communication technique.

The sensor and indicators need not be associated with identification information but could be provided in a device the sole purpose of which is to measure the concentration and provide an indication of it.

The device can be used in non-health care environments in which hand cleanliness is important or expected.

In a health-care environment, the device could be used by anyone who is providing services as well as by patients and their families or friends.

Information about the frequency, timing, and results of measurements performed historically by the user can be stored on the badge.

Many additional functions could be added to the badge by increasing the capacity of its processor, memory, displaying, communications ability, and user inputs features.

As shown in FIG. 6, in some examples, a monitor 70 could be mounted on a wall 72 of a space 74, such as a bathroom. The monitor could contain a radio frequency transceiver 75 that would cooperate with radio frequency identification (RFID) elements contained in badges of users. Using RFID technology, when a person wearing a badge passes near to the monitor, the monitor could use RF communication to determine that the person is present and to fetch information from the badge about the person's identity (and other information as discussed later). The monitor could also send an instruction to the badge to cause the badge to reset itself to the not disinfected state. Communication technologies other than RFID could also be used to detect the presence of the user and to communicate information between the monitor and the badge or other elements worn by the user. The element worn by the user could be one that identifies the user or one that does not identify the user.

When the person wearing the badge enters the bathroom, or any other monitored space such as a patient room, or a surgical theater, the triggering device sends a signal to the badge that causes the badge to enter the not disinfected state and light the lamp that indicates that state. This triggering will encourage the user to disinfect his hands before leaving the bathroom or before proceeding further into the monitored space in order to avoid the social disapproval associated with leaving the bathroom with the red light on. In these examples, the badge's state could be forced to change to the not disinfected state regardless of how much time has passed since the most recent successful test using the badge sensor. The user can be reset to the disinfected state by the user cleaning his hands and testing them.

As shown in FIG. 7, a hand cleanliness monitor 70 could include not only an ethanol or other sensor 106 but also a presence detector 108 and one or more indicators 110 of hand cleanliness with respect to one or more people who have entered the space. One of the indicators 112, which could be broadly visible to people in the space (for example, if it is placed on an interior wall of a room) or people outside the space (for example, if it is placed on an interior wall of a room) or both, could turn from green (indicating that all people in the space are believed to have disinfected hands) to red when a person is detected as entering the space. In that case, the red light would indicate to viewers that a person whose hand cleanliness state is unknown and assumed to be not disinfected has entered the space.

The person entering the room could cause the light to turn from red back to green by touching the sensor (assuming his hands bear enough ethanol to imply a disinfected condition) or by first cleaning his hands and then touching the sensor.

In some examples, the monitor could be placed on in interior wall of a patient's room. Whenever anyone enters the room, including health care workers, the patient, or guests, the monitor would indicate a possibly not disinfected condition until someone touches the sensor and causes the red light to turn green. Social pressure of people in the room, who would observe the red light would help to enforce good cleanliness habits on every person entering the room.

The parts of the monitor need not be included in a single integrated wall unit. For example, a portion of the monitor that detects that a person has entered or left a space could be a separate system, including an existing system, that would exchange the information with the monitor as needed. The indicators could also be located separately from the monitor to make the lights visible to many people even though the monitor is located near an entrance to or exit from a monitored space. The sensor, too, could be located separately from the monitor. For example, the badge sensors could provide the re-test information to the monitor.

In some examples, an entire building could be monitored by providing monitors on the walls at all entrances to the building. In addition to the social pressure associated with public display of the not disinfected condition, an employee or automated gate at each entrance could require that the person entering either prove that his hands are disinfected by using the sensor either upon entry or after using a disinfectant available at the entrance.

A variety of spaces could be monitored, including bathrooms (or other locations where disinfecting is especially important) and changing areas in hospitals or food processing facilities, for example.

In some examples, the monitor could include circuitry that would detect, in other ways than described above) a presence of one or more people within a space (whether or not the people have entered or left the space), would determine a cleanliness state of hands of the people detected as present, would include circuitry to report the cleanliness state.

A publicly viewable monitor used to indicate the disinfected condition for people within a space can facilitate social pressure being applied by people in a room to people who enter the room even without the monitor having any information about the identity of a person entering the room. In addition, the monitor may include or be part of a system that includes devices to determine who has entered a space and to correlate that information with a person who then uses the sensor to indicate that his hands have been disinfected.

For example, the person entering the room may carry a badge (of the kind issued by a health care facility) that uniquely identifies him and includes a bar code, a magnetic stripe, an RFID element, or another device that can be read by a reader 114 (for example, the RF transceiver 75 in FIG. 6) that is on the monitor or mounted separately on the wall. Depending on the technology, the user's badge could be read from a distance or be swiped on a reader. When the person enters the room, his presence and identity are detected. At the time when he successfully completes a measurement by the sensor indicating that his hands have been disinfected, his identity is read again and compared with the identities of people who have entered the room and not been determined to have passed a measurement for disinfected hands. Only when all of the people who have entered the room have passed the test will the red light be switched to green.

An enterprise could issue temporary identification cards to every person who enters a building or other space and does not already have an identification badge for use with the system.

A variety of other techniques could be used to identify the person entering a space, including detection of biometric information (such as a voice print or a finger print or a facial print) or requiring a person to enter an identification code on a keypad 116 on the monitor. The person could enter the identification both upon entering the room (in some cases as a trigger for a locked door or other entry gate) and upon passing a disinfection test using the monitor. In some implementations, it may be possible to identify a person using a fingerprint detection technique at the same location on the monitor and at the same time as the disinfection test is performed. Other techniques could also be used to assure that a successful test is accurately correlated to an identifiable person.

The monitor can also include circuitry that keeps track of how many people are in the space (for example, by also detecting when someone has left the space). When the oldest successful disinfection test (among tests that number as many as there are people still in the room) occurred more than a predetermined period (say 2 hours) earlier, the monitor can time out and change the green light to red until someone in the room successfully tests his hands again.

In these examples, and others, it is possible for people to deceive the monitor, for example, by having one person in the room repeatedly test his hands positively on behalf of other people in the room. However, as indicated earlier, at least in some examples, the social pressure associated with the public display of the disinfection state of the space and the shifting of green to red in certain situations, may be sufficient to significantly improve the frequency and quality of hand cleaning among people in the space.

Other arrangements could be used to reduce the degree and nature of the deception that may be possible and to increase the ability of a monitoring system to track and report the performance of identified people or groups of people in maintaining hand cleanliness. Some such arrangements would use the unique identifiers associated with different people to track their performance.

For example, the wall monitor could include a processor and software to track individuals who enter and leave a room based on their unique identifiers and correlate the identities with tests that are performed successfully. The monitor could then control the red light and green light based on the successful testing of hand cleanliness by each individual in the space at least as often as some pre-specified time period (say every two hours). By including a small display 120 on the face of the monitor, the person whose hand cleanliness requires re-testing can be identified by name or identifier or some other indicator. In this way, each of the people in the space can be alerted from time to time of the need to re-clean, and re-test and everyone in the space can know who needs to do so.

Such a monitor could be used in conjunction and cooperation with worn badges, for example, of the kind discussed earlier. For example, using RFID or wireless or other kinds of communication capability in the monitor and at least some badges, the monitor and the badge could communicate, exchange information, control actions, and make reports, all in a wide variety of ways.

In a simple example, the monitor could cause the light on a badge to switch from red to green at the same time (or different times) as the lights are switched on the monitor, to indicate to others in the space which person in the space needs to re-clean and re-test. A successful test performed on the badge can be reported to the monitor for use, for example, in the same way that a test on the monitor would be used. Conversely, the monitor can report to a badge a successful (or unsuccessful test) performed on the monitor by the owner of the badge. More generally, the badges and monitors in one or more spaces can continually be synchronized to store common information about tests by the owner of the badge and to cause common indications of the cleanliness state of the badge owner to be given by both the monitor and the badge.

As a person moves around in a building that has more than one monitored space, the monitors and the badges will together in that way maintain current information and provide current indications of the cleanliness state of the badge owner.

As shown in FIG. 9, although this co-operative maintenance of information and reporting can be done informally and by ad hoc action of different pairs of badges and monitors over time through a building, additional functions and better performance may be achieved by arranging for a portion or all of the monitors 130 in a building 132 or campus of buildings 134 to be interconnected by a wired or wireless communication network on a peer-to-peer basis or with the co-operation or control of a central server 136 or a distributed set of central servers 136, 138, 140. The central server or servers may be servers already used for a facility to provide communication and manage the control of other kinds of devices scattered throughout the facility or the reporting of information from other kinds of devices.

The monitors, the badges, and/or the central server or servers may include memory or mass storage 144 that contains a database 146 or other organized information about the permanently or temporarily registered people who have access to a building or space. The database can store information that is associated with individuals and information that is statistically relate to groups and subgroups of the individuals.

In some implementations, an individual badge can maintain a small database of information about a complete history of an individual's cleanliness testing beginning at the time when the badge was first issued, or at some later time. Or a rolling set of data ending at the current time may be kept. The data may catalog every instance when the user tested the cleanliness of his hands, the result, the time of the test, and the parameter values that were produced by the sensor in the testing. When the badge is able to communicate with monitors in different spaces or subspaces, the badge database may also track the places in which each of the tests was performed, which other people were present in the space when the tests were performed, and other information. Information in the badge database can be uploaded to one or more monitors using the communication links to the monitors, or may be uploaded from the badges directly to a central server using special badge readers located in one or more places in the facility.

Each monitor can maintain a database of information using information from badges of people with whom the monitor has interacted and information from other monitors in other spaces (for example, contiguous spaces). The database of a monitor could track every time a person has entered a monitored space and every time she has left the space. The data could include the time of entry, the time of exit, the space in which the user was most recently monitored, the time between entry into the space and when a re-test was performed, the results of the re-test, the number of re-tests performed in the room, the identities of other people in the room at the time of re-test, and a wide variety of other information.

If a person leaves a monitored space 131 and enters a monitored space 132, the monitors in the two spaces could be arranged to communicate so that the monitor in space 132 need not require a re-test if a re-test had been done in space 131 within a pre-specified earlier period.

When the monitors and/or badges are networked with a central server, the central server can use information provided from the monitors and/or badges to track the overall cleanliness testing activity of all of the monitored people in all spaces that are networked.

The central server could maintain a database 134 that could include detailed historical information and statistical summaries of information. The information could track every time any of the monitored people enters or leaves a monitored space, the number of times and the times at which re-testing has been done, the results of each re-test, the routes of the people moving through the building or campus, whether the people are wearing their badges, whether they used their badges or the wall monitors to re-test cleanliness, and a wide variety of other information.

The central server can use software 140 running on the server or servers to analyze information stored in the central database or the databases of one or more of the badges or the monitors. The analyses can address the performance of different groups on cleanliness, the correlation of cleanliness to location, the correlation of demographics (age, gender, geographic location) with cleanliness, the impact of training, monitoring, and other actions on the cleanliness performance, and time dependent changes by individuals, groups, and subgroups of cleanliness performance.

In addition to monitoring and analyzing information about cleanliness performance the central service can provide reports that are useful to or required by the party that operates the building or campus, other institutions, liability carriers, and governmental bodies that regulate certain aspects of the performance of the party and the individuals employed by the party. For example, governmental agencies may require hospitals to assure that hospital employees are disinfecting their hands more often than a certain number of times a day and to report failures to meet that requirement. Reports may also be given to individuals being monitored to groups of individuals, to their supervisors, and to others. Reporting to individuals can be done by email. For example, a doctor who is not disinfecting his hands often enough would periodically be sent an automatic email urging him to improve his cleanliness practices.

The invention claimed is:

1. A system comprising:
    an apparatus comprising:
        an electronic sensor configured to be carried by a person and to be used by the person to detect a cleanliness state of the person's hands,
        an indicator of hand cleanliness on an exterior portion of the apparatus, and
        a holder for the electronic sensor, the holder having a structure to temporarily receive an identification badge of the person; and
    a monitor installed in a space, the monitor configured to communicate with the apparatus, the monitor comprising a presence detector and one or more indicators of hand cleanliness with respect to one or more people who have entered the space
    wherein the one or more indicators of hand cleanliness are configured to indicate hand cleanliness only if all people in the space are believed to have disinfected hands.

2. The system of claim 1, wherein the monitor is mounted on a wall of the space.

3. The system of claim 2, wherein the monitor is mounted on a wall of the space such that at least one of the one or more indicators of hand cleanliness is visible to people outside the space.

4. The system of claim 1, wherein the one or more indicators of hand cleanliness are controlled in response to a signal from the apparatus.

5. The system of claim 2, wherein the monitor is mounted on a wall of the space such that at least one of the one or more indicators of hand cleanliness is visible to people inside the space.

6. The system of claim 2, wherein the monitor is a single integrated wall unit.

7. The system of claim 2, wherein a portion of the monitor that detects that a person has entered or left the space is located separated from the one or more indicators of hand cleanliness.

8. The system of claim 1 comprising monitors on the walls at all entrances to a building.

9. The system of claim 8, comprising an automated gate at each entrance configured to require that a person entering the building prove that his hands are disinfected by using the sensor.

10. A system comprising:
- an apparatus comprising an electronic sensor configured to be carried by a person and to be used by the person to detect a cleanliness state of the person's hands and an indicator of hand cleanliness on an exterior portion of the apparatus; and
- a monitor installed in a space, the monitor configured to communicate with the apparatus, the monitor comprising a presence detector and one or more indicators of hand cleanliness with respect to one or more people who have entered the space;
- wherein the one or more indicators of hand cleanliness are configured to indicate hand cleanliness only if all people in the space are believed to have disinfected hands.

11. The system of claim 10, wherein the monitor is mounted on a wall of the space.

12. The system of claim 11, wherein the monitor is mounted on a wall of the space such that at least one of the one or more indicators of hand cleanliness is visible to people outside the space.

13. The system of claim 10, wherein the one or more indicators of hand cleanliness are controlled in response to a signal from the apparatus.

14. The system of claim 11, wherein the monitor is mounted on a wall of the space such that at least one of the one or more indicators of hand cleanliness is visible to people inside the space.

15. The system of claim 11, wherein the monitor is a single integrated wall unit.

16. The system of claim 11, wherein a portion of the monitor that detects that a person has entered or left the space is located separated from the one or more indicators of hand cleanliness.

17. The system of claim 10 comprising monitors on the walls at all entrances to a building.

18. The system of claim 17, comprising an automated gate at each entrance configured to require that a person entering the building prove that his hands are disinfected by using the sensor.

* * * * *